United States Patent

Kasai et al.

Patent Number: 5,344,938
Date of Patent: Sep. 6, 1994

[54] INDOLE 3-CARBOXYLIC ACID DERIVATIVES

[75] Inventors: Masaji Kasai, Kanagawa; Hitoshi Arai; Hiroshi Nishikawa, both of Shizuoka; Takehiro Ogasa; Masahiko Kinugawa, both of Osaka; Shinji Tomioka, Wakayama, all of Japan

[73] Assignee: Kyowa Hakko Kogyo Co., Ltd., Tokyo, Japan

[21] Appl. No.: 41,180

[22] Filed: Apr. 1, 1993

[30] Foreign Application Priority Data

Apr. 7, 1992 [JP] Japan ................................. 4-85276

[51] Int. Cl.$^5$ .......................................... C07D 209/42
[52] U.S. Cl. ........................... 548/492; 548/493
[58] Field of Search .............................. 548/492

[56] References Cited
FOREIGN PATENT DOCUMENTS
WO87/06227 10/1987 European Pat. Off. .

OTHER PUBLICATIONS

J. Prakt Chem., 311 (5), 807 (1969).
Chemical Abstract, vol. 9, 2868n (1968).
Chemical Abstract, vol. 70, 47295K (1969).
Chemical Abstract, vol. 109, 92188n (1988).
Chemical Abstract, vol. 115, 135866a (1991).

Primary Examiner—David B. Springer
Attorney, Agent, or Firm—Nixon & Vanderhye

[57] ABSTRACT

An indole derivative represented by formula (I):

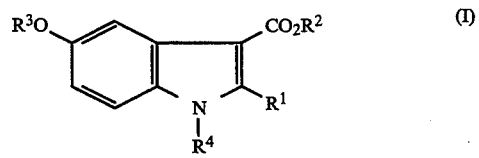

wherein $R^1$ is a lower alkoxymethyl group or a formyl group, $R^2$ is a lower alkyl group, $R^3$ is a hydrogen atom or a lower alkyl group and $R^4$ is a hydrogen atom or a lower alkyl group, which is useful as an intermediate for the synthesis of a compound, 5-aziridino-3-hydroxymethyl-1-methyl-2- (1H-indole-4,7-dione)prop-$\beta$-ene-$\alpha$-ol, which has antitumor activity.

2 Claims, No Drawings

INDOLE 3-CARBOXYLIC ACID DERIVATIVES

FIELD OF THE INVENTION

The present invention relates to a novel indole derivative useful as an intermediate for the synthesis of a compound, 5-aziridino-3-hydroxymethyl-1-methyl-2-(1H-indole-4,7-dione)prop-β-ene-α-ol (WO87/06227), which has antitumor activity.

BACKGROUND OF THE INVENTION

Various indole derivatives have been disclosed including those having a hydroxyl group at the 5-position, an alkoxycarbonyl group or a carboxyl group at the 2- and 3-positions and an alkyl group or an aryl group at the 1-position (Chem. Abst., 69, 2868n (1968); J. Prakt. Chem., 311(5), 807 (1969); and Chem. Abst., 70, 47295k (1969)) and having a hydroxyl group or a methoxy group at the 5-position, a 1-phenylethyl group at the 1-position and a methoxycarbonyl group at the 2- and 3-positions (Chem. Abst., 109, 92188n (1988)). Also disclosed are those indole derivatives having a bromine atom at the 6-position, a methyl group at the 1-position, a hydroxyl group or an acetoxy group at the 5-position, a hydrogen atom or an aminomethyl group at the 4-position, an ethoxycarbonyl group at the 3-position and a substituted or unsubstituted phenoxymethyl group at the 2-position (Chem. Abst., 115, 135866a (1991)).

SUMMARY OF THE INVENTION

An object of the present invention is to provide indole derivatives useful as an intermediate for the synthesis of a compound, 5-aziridino-3-hydroxymethyl-1-methyl-2-(1H-indole-4,7-dione)prop-β-ene-α-ol, which has an antitumor activity, represented by the following formula (I):

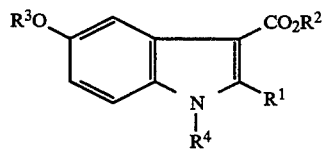

wherein $R^1$ is a lower alkoxymethyl group or a formyl group, $R^2$ is a lower alkyl group, $R^3$ is a hydrogen atom or a lower alkyl group and $R^4$ is a hydrogen atom or a lower alkyl group.

The indole derivative represented by the formula (I) will be called "compound (I)" hereinafter. Other compounds will also be referred to in the same manner according to their formula numbers.

DETAILED DESCRIPTION OF THE INVENTION

With regard to the definition of groups in the formula (I), the alkyl moiety of the lower alkyl and lower alkoxymethyl groups may be a linear or branched alkyl moiety having 1 to 4 carbon atoms, such as methyl, ethyl, propyl, isopropyl, butyl, isobutyl, sec-butyl and tert-butyl.

A process for the production of the compound (I) is described below.

The compound (I) can be produced in accordance with the following reaction steps (1) to (3):

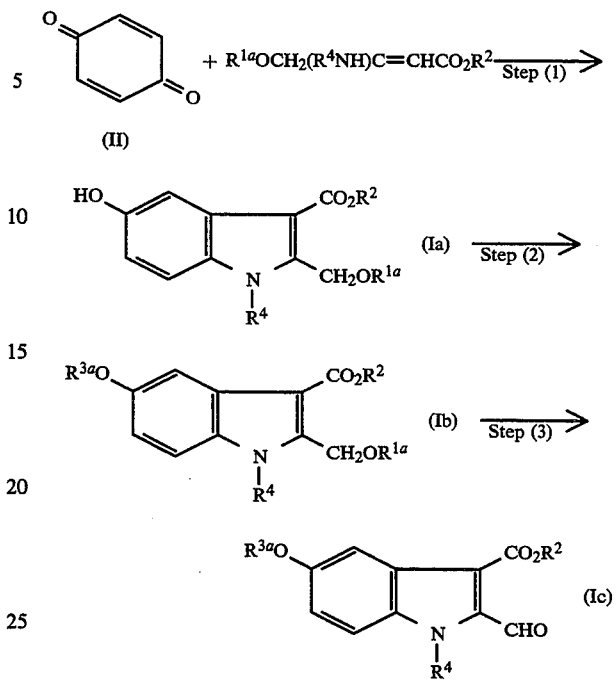

wherein each of $R^{1a}$ and $R^{3a}$ is a lower alkyl group, and $R^2$ and $R^4$ are the same groups as defined above.

Step (1)

The compound (Ia) in which the $R^1$ group is a lower alkoxymethyl may be obtained by condensing 1,4-benzoquinone (II) with the compound (III) in an inert solvent in the presence or absence of an organic acid or in the presence or absence of a Lewis acid. The organic acid or the Lewis acid may be used in an amount of a catalytic amount to 10 moles, preferably 0.3 to 3 moles, per mole of the compound (II). Examples of the organic acid include acetic acid, propionic acid, formic acid, trifluoroacetic acid or the like. Examples of the Lewis acid include a boron trifluoride-diethyl ether complex, zinc chloride or the like. Examples of the inert solvent include ethers such as diethyl ether, tetrahydrofuran and the like, and esters such as ethyl acetate, propyl acetate, butyl acetate and the like. The reaction may be completed generally within 1 to 48 hours at a temperature of 0° to 70° C.

Step (2)

The compound (Ib) in which the $R^3$ group is a lower alkyl and the $R^4$ group is also a lower alkyl may be obtained by allowing the compound (Ia) prepared in the above step (1) to react with 1 to 5 equivalent amounts of a lower alkyl halide in an inert solvent at 0° to 50° C. for 1 to 24 hours in the presence of an equivalent or excess amount of a base. In this instance, examples of the halogen in the lower alkyl halide include chlorine, bromine and iodine. Examples of the base include sodium hydride, potassium hydride, sodium carbonate, potassium carbonate, sodium ethoxide, sodium methoxide, potassium t-butoxide, sodium t-butoxide and the like, and examples of the inert solvent include dimethylformamide, dimethyl sulfoxide, tetrahydrofuran, dimethoxyethane and the like.

Step (3)

The compound (Ic) in which the $R^1$ group is a formyl may be obtained by allowing the compound (Ib) prepared in the above step (2) to react with 1 to 5 equivalent amounts of an oxidizing agent in an inert solvent. Examples of the oxidizing agent include 2,3-dichloro-5,6-dicyanobenzoquinone (DDQ), N-bromosuccinimide and the like, as well as copper (II) nitrate adsorbed to silica gel. Examples of the inert solvent include toluene, carbon tetrachloride, dioxane, chloroform, methylene chloride, dichloroethane and the like or a mixture of the solvent and water or two-phase systems with water. The reaction may be completed in general within 0.5 to 24 hours at 0° C. to the boiling point of the used solvent.

In each reaction step, the concentration of the main reactant in the solvent is adjusted to 1 to 100 w/v%, preferably 3 to 20 w/v%.

Each of the compounds obtained in the above steps (1) to (3) may be isolated and purified by a conventional method in the field of organic synthetic chemistry, such as filtration, extraction, washing, drying, concentration, recrystallization, various chromatographic techniques and the like. When the compound is used as an intermediate, it can be subjected to the subsequent reaction step without purification.

The following Examples and Reference Examples are provided to further illustrate the present invention. It is to be understood, however, that the examples are for purpose of illustration only and are not intended to limit the invention.

In the following Examples, physicochemical properties of each compound were measured using the following instruments.

Melting point: Buchi 535

MS: JEOL JMS-D300 (Japan Electron Optics Laboratory Co., Ltd.), M-80B (Hitachi Ltd.) (measured by EI method).

$^1$H NMR: R-90H (90 MHz); JEOL JNM-GX270 (270 MHz); AC-300 (300 MHz) (Bruker)

IR: FT-200 (Horiba) (measured by KBr method)

Elemental analysis: 2400CHN Elemental Analyser Perkin-Elmer

EXAMPLE 1

5-Hydroxy-3-methoxycarbonyl-2-methoxymethyl-1-methylindole

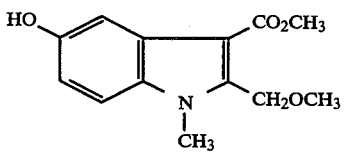

3.1 g of 1,4-benzoquinone (28.7 mmol) was dissolved in 50 ml of acetic acid to which was subsequently added dropwise 2.28 g (14.3 mmol) of methyl 4-methoxy-3-methylamino-2-butenoate and the mixture was stirred for 5 hours at room temperature. After the solvent was distilled off under reduced pressure, the resulting residue was dissolved in ethyl acetate, washed with water and saturated sodium chloride aqueous solution and then dried over anhydrous magnesium sulfate. After anhydrous magnesium sulfate was filtered off and the solvent was distilled off under reduced pressure, the residue was purified by a silica gel column chromatography (eluent: hexane-ethyl acetate, 2:1) to obtain 0.78 g of the title compound with a yield of 22%.

Melting point: 168.5°–170.4° C.

MS: m/z 249 (M+), $C_{13}H_{15}NO_4$=249.27.

$^1$H NMR (90 MHz, CDCl$_3$/DMSO-d$_6$): δ (ppm) 7.60 (1H, d, J=2.4), 7.18 (1H, d, J=8.8), 7.13 (1H, brs), 6.88 (1H, dd, J=8.8, 2.4), 5.08 (2H, s), 3.91 (3H, s), 3.77 (3H, s), 3.38 (3H, s)

IR: cm$^{-1}$ 3301, 1662, 1624, 1531, 1486.

Elemental analysis (%): Found C=62.23, H=6.08, N=5.50 Calcd. C=62.64, H=6.07, N=5.62

EXAMPLE 2

5-Methoxy-3-methoxycarbonyl-2-methoxymethyl-1-methylindole

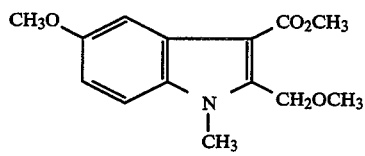

14.9 g of 5-hydroxy-3-methoxycarbonyl-2-methoxymethyl-1-methylindole (59.8 mmol) obtained in Example 1 was dissolved in 150 ml of anhydrous dimethylformamide, and the solution was stirred in a stream of nitrogen under ice cooling. To this were added 2.63 g (65.8 mmol) of sodium hydride (60% oil dispersion) and 4.1 ml (65.9 mmol) of methyl iodide in that order. After 2 hours of heating at 50° C., the resulting reaction mixture was cooled down, mixed with water and then extracted with ethyl acetate. The ethyl acetate layer was washed with water and saturated sodium chloride aqueous solution and then dried over anhydrous magnesium sulfate. After anhydrous magnesium sulfate was filtered off and the solvent was distilled off under reduced pressure, the resulting residue was purified by a silica gel column chromatography (eluent: hexane-ethyl acetate, 3:1) to obtain 14.1 g of the title compound with a yield of 89%.

Melting point: 89.2–91.0° C.

MS: m/z 263 (M+), $C_{14}H_{17}NO_4$=263.30.

$^1$H NMR (90MHz, CDCl$_3$): δ (ppm) 7.65 (1H, d, J=2.4), 7.24 (1H, d, J=9.0), 6.94 (1H, dd, J=9.0, 2.4), 5.09 (2H, s), 3.94 (3H, s), 3.89 (3H, s), 3.80 (3H, s), 3.38 (3H, s).

IR: cm$^{-1}$ 1685, 1522, 1491.

Elemental analysis (%): Found C=63.97, H=6.74, N=5.26 Calcd. C=63.86, H=6.51, N =5.32

EXAMPLE 3

5-Hydroxy-3-methoxycarbonyl-2-methoxymethyl-1H-indole

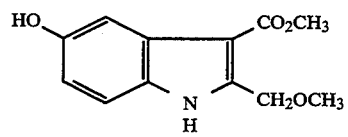

32.4 g (300 mmol) of 1,4-benzoquinone was dissolved in 200 ml of ethyl acetate, 200 ml (350 mmol) of acetic acid was added thereto, followed by dropwise addition of 14.5 g (100 mmol) of methyl 4-methoxy-3-amino-2-butenoate. With stirring, the reaction mixture was heated for 15 hours while keeping the inner temperature at 50° C. To this was then added dropwise 200 ml of an aqueous solution containing 52.2 g (300 mmol) of sodium hydrosulfite. The mixture was further stirred at room temperature for 2 hours while controlling the reaction mixture within a pH range of from 4.5 to 7.5 with 5 N sodium hydroxide. Thereafter, crystals thus precipitated were collected by filtration and washed with ethyl acetate to obtain 7.33 g of crude crystals. The filtrate and the washings were combined and then allowed to separate into organic and water layers. The water layer was extracted with 50 ml of ethyl acetate, and the resulting ethyl acetate layer was combined with the organic layer. The thus combined organic layer was washed with saturated sodium chloride aqueous solution and then dried over anhydrous magnesium sulfate. After anhydrous magnesium sulfate was filtered off and the solvent was distilled off under reduced pressure, the resulting residue was purified by an alumina column chromatography (eluent: ethyl acetate). Main fractions thus obtained were concentrated, and the concentrated residue was slurried with 150 ml of ethyl acetate. The thus obtained crude product was combined with the crude crystals previously collected by filtration, and the combined product was recrystallized from 260 ml of ethyl acetate to obtain 10.5 g of the title compound with a yield of 44.2%.

Melting point: 160.0° C. (decomposition).

MS: m/z 235 (M+), $C_{12}H_{15}NO_4=235.27$.

$^1$H NMR (300 MHz, DMSO-$d_6$): δ (ppm) 11.74 (1H, s), 8.97 (1H, s), 7.34 (1H, d, J=2.4), 7.25 (1H, d, J=8.6), 6.78 (1H, dd, J=8.6, 2.4), 4.91 (2H, s), 3.81 (3H, s), 3.39 (3H, s).

IR: cm$^{-1}$ 3340, 3310, 1664, 1479, 1464, 1233, 1170.

Elemental analysis (%): Found C=61.11, H=5.79, N=5.80 Calcd. C=61.27, H=5.57, N=5.95

EXAMPLE 4

5-Methoxy-3-methoxycarbonyl-2-methoxymethyl-1-methylindole 22.5 g (100 mmol) of 5-hydroxy-3-methoxycarbonyl-2-methoxymethyl -1H-indole obtained in Example 3 was dissolved in 235 ml of anhydrous dimethylformamide, followed by the addition of 56.8 g (400 mmol) of methyl iodide at room temperature. To this was added 44.9 g (400 mmol) of potassium t-butoxide gradually by dividing the measured amount into 5 portions under ice cooling. The reaction mixture was warmed up to room temperature and stirred for 1 hour. After ice cooling again, 940 ml of water was added dropwise to the reaction to keep the inner temperature not more than 20° C. The mixture was stirred for another 1 hour under ice cooling. Crystals thus precipitated were collected by filtration, washed with 80 ml of water and then dried under reduced pressure to obtain 23.2 g of the title compound with a yield of 87%. The compound thus obtained showed the same properties as those of the compound obtained in Example 2 in terms of NMR, IR and TLC data.

EXAMPLE 5

2-Formyl-5-methoxy-3-methoxycarbonyl-1-methylindole

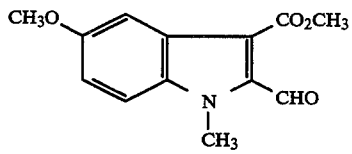

5.0 g (19.0 mmol) of 5-methoxy-3-methoxycarbonyl-2-methoxymethyl -1-methylindole obtained in Example 2 or 4 was dissolved in 200 ml of anhydrous toluene, followed by the addition of 4.94 g (20.9 mmol) of DDQ and subsequent 2 hours of heating under reflux. After cooling the reaction mixture and removing impurities by filtration, the organic layer was washed with water and saturated sodium chloride aqueous solution and then dried over anhydrous magnesium sulfate. After anhydrous magnesium sulfate was filtered off and the solvent was distilled off under reduced pressure, the resulting residue was purified by a silica gel column chromatography (eluent: hexaneethyl acetate, 3:1) to obtain 3.38 g of the title compound with a yield of 72%.

Melting point: 133.1–133.5° C.

MS: m/z 247 (M+), $C_{13}H_{13}NO_4=247.25$.

$^1$H NMR (90 MHz, CDCl$_3$): δ (ppm) 10.76 (1H, s), 7.66 (1H, d, J =2.4), 7.34 (1H, d, J=9.0), 7.11 (1H, dd, J=9.2, 2.4), 4.10 (3H, s), 4.00 (3H, s), 3.91 (3H, s).

IR: cm$^{-1}$ 1693, 1664, 1506, 1495.

Elemental analysis (%): Found C=62.88, H=5.31 N=5 68 Calcd. C=63.15, H=5.30, N=5.67

EXAMPLE 6

2-Formyl-5-methoxy-3-methoxycarbonyl-1-methylindole 24.7 g (100 mmol) of 5-methoxy-3-methoxycarbonyl-2-methoxymethyl -1-methylindole obtained in Example 2 or 4 was dissolved in 494 ml of methylene chloride and 27.4 ml of water, followed by the addition of 25.0 g (110 mmol) of DDQ and subsequent 8 hours of stirring at 30° C. The reaction mixture was filtered and the thus collected insoluble materials were washed with 120 ml of methylene chloride. The filtrate and the washings were combined and applied to a column packed with 123.5 g of alumina. The eluate was combined with another eluate obtained by further elution of the alumina column with 2,260 ml of methylene chloride, and the thus combined eluates were concentrated under reduced pressure. The thus obtained residue was recrystallized from 111 ml of ethyl acetate, and the precipitated crystals were collected by filtration and dried under reduced pressure to obtain 11.8 g of the title compound with a yield of 80.1%. The compound thus obtained showed the same properties as those of the compound obtained in Example 5 in terms of NMR, IR and TLC data.

REFERENCE EXAMPLE 1

Ethyl 5-methoxy-3-methoxycarbonyl-1-methyl 2-indole acrylate

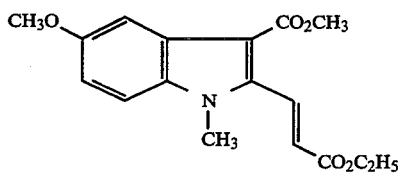

3.18 ml (15.9 mmol) of triethyl phosphonoacetate was dissolved in 10 ml of anhydrous tetrahydrofuran. The solution was mixed with 578 mg (14.5 mmol) of sodium hydride (60% oil dispersion) in a stream of nitrogen under ice cooling, and the mixture was stirred for 15 minutes. To this was added dropwise 90 ml of anhydrous tetrahydrofuran containing 3.25 g (13.1 mmol) of 2-formyl-5-methoxy-3-methoxycarbonyl -1-methylindole obtained in Example 5. The resulting mixture was stirred for 1 hour in a stream of nitrogen under ice cooling. To the resulting reaction mixture were added water and ethyl acetate, and the resulting organic layer was washed with water and saturated sodium chloride aqueous solution and then dried over anhydrous magnesium sulfate. After anhydrous magnesium sulfate was filtered off and the solvent was distilled off under reduced pressure, crystals thus precipitated were slurried with diethyl ether and dried to obtain 3.74 g of the title compound with a yield of 90%.

Melting point: 109.0–109.6° C.

MS: m/z 317 (M+), $C_{17}H_{19}NO_5 = 317.35$.

$^1$H NMR (90 MHz, CDCl$_3$): δ (ppm) 8.38 (1H, d, J=16.7), 7.66 (1H, d, J=2.4), 7.26 (1H, d, J=9.0), 6.99 (1H, dd, J=9.1, 2.5), 6.39 (1H, d, J=16.7), 4.31 (2H, q, J=7.2), 3.95 (3H, s), 3.90 (3H, s), 3.84 (3H, s), 1.37 (3H, t, J=7.0).

IR: cm$^{-1}$ 1707, 1689, 1626, 1477.

Elemental analysis (%): Found C=64.26, H=6.18, N=4.40

Calcd. C=64.34, H=6.03, N=4.41

REFERENCE EXAMPLE 2

Ethyl 5-methoxy-3-methoxycarbonyl -1-methyl-4-nitro-2-indole acrylate

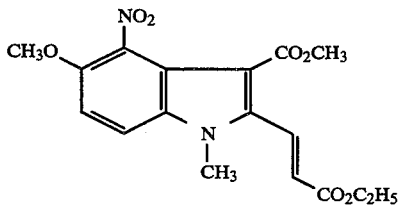

200 mg (0.63 mmol) of ethyl 5-methoxy-3methoxycarbonyl-1-methyl-2-indole acrylate obtained in Reference Example 1 was dissolved in 3 ml of acetic acid. To the solution was added dropwise 1.5 ml of acetic acid containing 31 μl of fuming nitric acid with stirring under cooling, followed by 1 hour of stirring at room temperature. To the thus obtained reaction solution were added water and ethyl acetate, and the resulting organic layer was washed thoroughly with water and then with saturated sodium chloride aqueous solution, followed by drying over anhydrous magnesium sulfate. After anhydrous magnesium sulfate was filtered off and the solvent was distilled off under reduced pressure, crystals thus precipitated were slurried with diethyl ether and dried to obtain 184 mg of the title compound with a yield of 81%.

Melting point: 193.2–194.9° C.

MS: m/z 362 (M+), $C_{17}H_{18}N_2O_7 = 62.34$.

$^1$H NMR (90 MHz, CDCl$_3$): δ (ppm) 8.10 (1H, d, J=16.5), 7.44 (1H, d, J=9.0), 7.10 (1H, d, J=9.2), 6.47 (1H, d, J=16.7), 4.31 (2H, q, J=7.1), 3.94 (3H, s), 3.84 (3H, s), 3.82 (3H, s), 1.36 (3H, t, J=7.2).

IR: cm$^{-1}$ 1714, 1630, 1537, 1485.

Elemental analysis (%): Found C=56.31, H=5.03, N=7.62 Calcd. C=56.35, H=5.01, N=7.73.

REFERENCE EXAMPLE 3

Methyl 5-methoxy- 3-methoxycarbonyl-1-methyl-4-nitro-2-indole acrylate

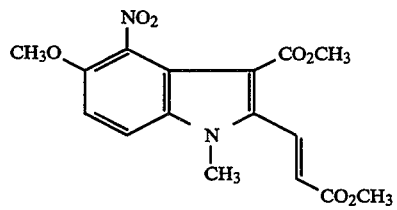

70 mg (0.19mmol) of ethyl 5-methoxy-3-methoxycarbonyl-1-methyl -4-nitro-2-indole acrylate obtained in Reference Example 2 and 42 mg (0.22 mmol) of sodium methoxide were dissolved in 80 ml of anhydrous methanol, and the resulting mixture was heated under reflux for 2 hours. After cooling the reaction mixture, crystals thus precipitated were collected by filtration, washed with methanol, water and methanol in that order and then dried to obtain 39 mg of the title compound with a yield of 59%.

$^1$H NMR (270 MHz, DMSO-d6): δ (ppm) 8.03 (1H, d, J=16.3), 7.93 (1H, d, J=8.9), 7.40 (1H, d, J=9.4), 6.66 (1H, d, J=16.3), 3.93 (3H×2, s), 3.79 (3H, s), 3.67 (3H, s)

The compounds obtained in Reference Examples 2 and 3, namely ethyl 5-methoxy-3-methoxycarbonyl -1-methyl-4-nitro-2-indole acrylate and methyl 5-methoxy-3-methoxycarbonyl-1-methyl -4-nitro-2-indole acrylate (identical to the compound 16 disclosed in WO87/06227), can be used as intermediates for the synthesis of 5-aziridino-3-hydroxymethyl -1-methyl-2-(1-indole-4,7-dione)prop-β-ene-α-ol (EO9) which is an indoloquinone derivative having an antitumor activity.

Thus, in accordance with the present invention, novel indole derivatives which are useful as intermediates for the synthesis of pharmaceutical drugs.

While the invention has been described in detail and with reference to specific examples thereof, it will be apparent to one skilled in the art that various changes and modifications can be made therein without departing from the spirit and scope thereof.

What is claimed is:

1. A compound represented by formula (I):

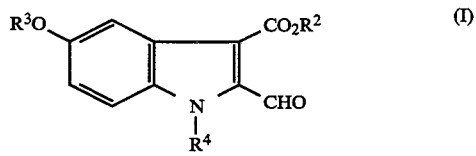

wherein $R^2$ is a lower alkyl group, $R^3$ is a lower alkyl group and $R^4$ is a lower alkyl group.

2. The compound according to claim 1, wherein $R^2$ is a methyl group $R^3$ is a methyl group and $R^4$ is a methyl group.

* * * * *